United States Patent [19]
Baker et al.

[11] Patent Number: 5,346,906
[45] Date of Patent: Sep. 13, 1994

[54] SUBSTITUTED PYRIDINES, THEIR PREPARATION, FORMULATIONS AND USE IN DEMENTIA

[75] Inventors: Raymond Baker, Much Hadham; John Saunders, Near Ware; Timothy M. Willson, Chelmsford; Janusz J. Kulagowski, Bishops Stortford, all of England

[73] Assignee: Merck Sharpe & Dohme Ltd., Hoddesdon, England

[21] Appl. No.: 976,795

[22] Filed: Nov. 16, 1992

Related U.S. Application Data

[63] Continuation of Ser. No. 798,852, Nov. 18, 1991, abandoned, which is a continuation of Ser. No. 564,491, Aug. 8, 1990, abandoned.

[51] Int. Cl.$^5$ .................... C07D 451/00; A61K 31/46
[52] U.S. Cl. .................... 514/305; 546/133; 546/137
[58] Field of Search ........... 546/133, 137; 514/305

[56] References Cited

U.S. PATENT DOCUMENTS

| | | | |
|---|---|---|---|
| 3,764,604 | 10/1973 | Ash et al. | 546/133 |
| 4,125,531 | 11/1978 | Yen | 546/133 |
| 4,179,510 | 12/1979 | McCall | 424/267 |
| 4,250,181 | 2/1981 | McCall | 424/250 |
| 4,921,860 | 5/1990 | Cliffe | 546/133 |

FOREIGN PATENT DOCUMENTS

| | | |
|---|---|---|
| 0094018 | 11/1983 | European Pat. Off. . |
| 239309 | 9/1987 | European Pat. Off. . |
| 1913732 | 2/1970 | Fed. Rep. of Germany . |
| 48-056687 | 8/1973 | Japan . |

OTHER PUBLICATIONS

Journal of Medicinal Chemistry, vol. 27, No. 9, Sep. 1974 pp. 1182–1185.
Chem. Absts. vol. 79, No. 19, Nov. 12, 1973, p. 346, Col. 2 Abstract 115448a.
Archiv Der Pharmazie, vol. 306, No. 12, Dec. 1973 pp. 934–942.
Chem. Absts. vol. 99, No. 14, Oct. 3, 1983, p. 216, Col. 1, Abstract 108875x.
Chem. Absts., vol. 107, No. 5, Aug. 3, 1987, p. 682 Col. 1, Abstract 39626m.
Chem. Absts., vol. 88, No. 25, Jun. 19, 1978, p. 738, Col. 1, Abstract 190548x.
Beilsteins Handbuch Der Organischen Chemie, 4th Ed. 3rd and 4th Suppl. Series, vol. 23, part 2, 1980, pp. 1022, 1023.
Beilsteins Handbuch Der Organischen Chemie, 4th Ed. 3rd and 4th Suppl. Series, vol. 23, part 4, 1980 p. 2509.
Beinsteins Handbuch Der Organischen Chemie, vol. 25, part 2 1981 pp. 806–808.
Chemische Berichte, vol. 95, No. 12, 1962, pp. 2896–2900.
Chemische Berichte, vol. 94, No. 2, 1961 pp. 407–412.
J. Med. Chem., 14, 554–556 (1971) (Cumulative).
Zh. Obshch. Khim 34, pp. 4104–4107 (1964), by Tadykow, et al.
J. Gen. Chem. USSR 33, (1963), by Tadykow, et al.
Chem. Absts. vol. 75 (1967), Abstract #36420Z.

*Primary Examiner*—Johann Richter
*Assistant Examiner*—Catherine Scalzo
*Attorney, Agent, or Firm*—Robert J. North; Melvin Winokur

[57] ABSTRACT

Pyridines, substituted by a quinuclidine and a substituent of low lipophilicity or a hydrocarbon substituent, their salts and prodrugs, and formulations thereof are useful in the treatment of neurodegenerative disorders such as dementia. The compounds can be synthesized by methods analogous to these known in the art.

8 Claims, No Drawings

SUBSTITUTED PYRIDINES, THEIR PREPARATION, FORMULATIONS AND USE IN DEMENTIA

CROSS REFERENCE TO RELATED APPLICATIONS

The instant case is a continuation case of U.S. Ser. No. 07/798,852 (Case Docket T-1064CA), filed Nov. 18. 1991, now abandoned, which in turn is a continuation case of U.S. Ser. No. 07/564,491 (Case T-1064), filed Aug. 8, 1990, now abandoned.

The present invention relates to a class of substituted pyridine compounds which stimulate central muscarinic acetylcholine receptors and therefore are useful in the treatment of neurological and mental illnesses whose clinical manifestations are due to cholinergic deficiency. Such diseases include presenile and senile dementia (also known as Alzheimer's disease and senile dementia of the Alzheimer type respectively), Huntington's chorea, tardive dyskinesia, hyperkinesia, mania and Tourette Syndrome. Alzheimer's disease, the most common dementing illness, is a slowly progressive neurological disorder characterised by marked deficits in cognitive functions including memory, attention, language and visual perception capabilities.

Published European Patent Application No. 239309 discloses a class of oxadiazole compounds having a substituent of low lipophilicity, which are useful in the treatment of neurodegenerative disorders. In J. Med. Chem. (1971) 14 (6), 554–556 are disclosed 3-hydroxy-3-(2-pyridinyl)-1-azabicyclo[2.2.2]octane and 3-(2-pyridinyl)-1-azabicyclo[2.2.21oct-2-ene as intermediates in the preparation of compounds evaluated for their nicotinic activity. The former compound was itself tested and found in some tests to perform as a weak nicotinic agonist, but in other tests not to perform as a nicotinic agonist. It has now been found that a class of pyridines, having a broader range of substituents, also stimulate cholinergic transmission. Some of these compounds also exhibit nicotinic activity.

It is possible that the enhancement of cholinergic transmission demonstrated by the compounds of this invention is achieved either directly by stimulating postsynaptic receptors, or indirectly by potentiating acetylcholine release.

The compounds of the present invention are pyridines substituted on one of the ring carbon atoms thereof with a non-aromatic azacyclic or non-fused azabicyclic ring system having more than 5 ring atoms and independently substituted on each of the other ring carbon atoms with a substituent of low lipophilicity or a hydrocarbon substituent provided that the non-aromatic ring is attached to the pyridine ring other than at its 2'-carbon position; and salts and prodrugs thereof, other than 3-hydroxy-3-(2-pyridinyl)-1-azabicyclo[2.2.2]octane and 3-(2-pyridinyl)-1-azabicyclo[2.2.2]oct-2-ene.

Accordingly, the present invention provides a compound of formula (I):

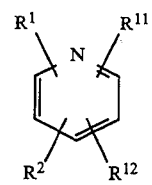

or a salt or prodrug thereof; wherein $R^1$ represents a non-aromatic azacyclic or non fused azabicyclic ring system having more than 5 ring atoms and provided that $R^1$ is attached to the pyridine ring other than at the 2'-carbon position of $R^1$; and $R^2$, $R^{11}$ and $R^{12}$ independently represent hydrogen, halo, —$CF_3$, —$OR^6$, —$NR^6R^7$, —$NHOR^6$, —$NHNH_2$, —CN, $COR^8$, or a substituted or unsubstituted, saturated or unsaturated hydrocarbon group; wherein $R^6$ is hydrogen, $C_{1-6}$ alkyl, $C_{2-6}$ alkenyl or $C_{2-6}$ alkynyl, $R^7$ is hydrogen, $C_{1-6}$ alkyl or —$COCH_3$, and $R^8$ represents —$OR^6$ or —$NR^6R^7$; other than 3-hydroxy-3-(2-pyridinyl)-1-azabicyclo[2.2.2]octane and 3-(2-pyridinyl)-1-azabicyclo[2.2.21]oct-2-ene.

The azacyclic or azabicyclic ring system is a non-aromatic ring system containing one nitrogen atom as the sole heteroatom. Suitably the ring system contains from 6 to 10 ring atoms, preferably from 6 to 8 ring atoms. Preferably, the ring system contains a tertiary amino nitrogen atom in a caged structure. The bicyclic systems may be spiro or bridged. Preferably, the nitrogen atom is at a bridgehead in a bicyclic system. Examples of suitable ring systems for the group $R^1$ include the following:

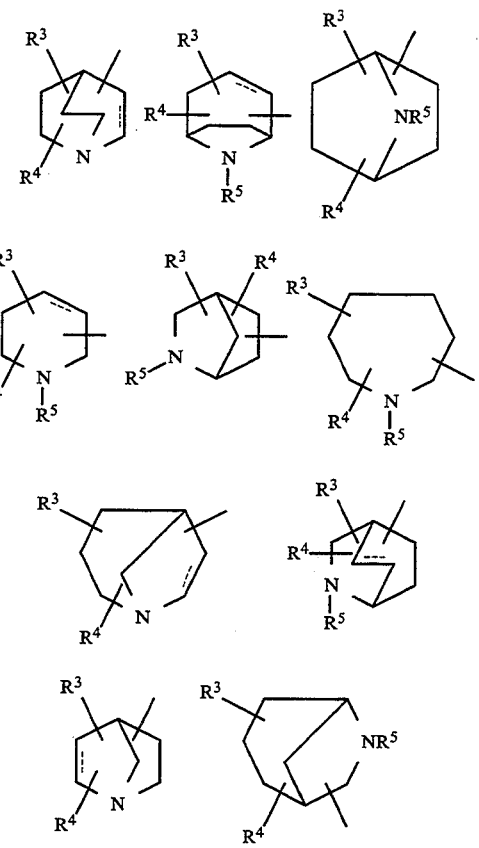

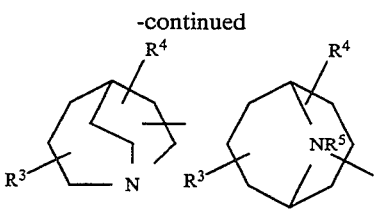

wherein the broken line represents an optional chemical bond;

the substituents $R^3$ and $R^4$ may be present at any position, including the point of attachment to the pyridine ring, and independently represent hydrogen, $C_{1-4}$ alkyl, halo, $C_{1-4}$ alkoxy, hydroxy, carboxy or $C_{1-4}$ alkoxycarbonyl; or $R^3$ and $R^4$ together represent carbonyl; and $R^5$ represents hydrogen or $C_{1-4}$ alkyl.

It will be appreciated that the nitrogen atom in the azacyclic or azabicyclic ring will carry a lone pair of electrons.

Suitably, the group $R^3$ is hydrogen or methyl; and $R^4$ is hydrogen, $C_{1-4}$ alkoxy, $C_{1-4}$ alkyl, $C_{1-4}$ alkoxycarbonyl, halo or hydroxy, preferably methoxy, methyl, fluoro, chloro, hydroxy or methoxycarbonyl. Preferably one or both of $R^3$ and $R^4$ is hydrogen. More preferably, $R^3$ is hydrogen and $R^4$ is hydrogen or methoxycarbonyl, especially hydrogen.

Preferably, the group $R^5$ represents hydrogen or methyl.

Suitably, the azacyclic or azabicyclic ring system is piperidine, tetrahydropyridine, azanorbornane, quinuclidine, isoquinuclidine, azabicyclo[2.2.2]octene or 1-azabicyclo[3.2.1]octane, any of which may be either unsubstituted or substituted with methyl, hydroxy, fluoro, chloro or methoxycarbonyl. Preferably, $R^1$ is quinuclidine, 1-azabicyclo[2.2.1]heptane or isoquinuclidine (especially quinuclidine) optionally substituted with methoxycarbonyl. Preferably, the azacyclic or azabicyclic ring is bonded at the 2- or 3-position of the pyridine ring, especially the 2-position.

When the groups $R^2$, $R^{11}$ and/or $R^{12}$ are hydrocarbon substituents, they may be $C_{1-5}$ alkyl, $C_{2-15}$ alkenyl, $C_{2-15}$ alkynyl, aryl or aralkyl. The alkyl, alkenyl or alkynyl groups may be straight, branched or cyclic groups. Suitably, the alkyl group comprises from 1 to 6 carbon atoms. The hydrocarbon group(s) may carry one or more substituents. Suitable substituent groups include halo, —$OR^6$, —$CF_3$, —$NR^6R^7$, —$NO_2$, optionally substituted aryl keto —$SR^6$, —$SOR^6$, —$SO_2R^6$, —$CO_2R^6$ and —$CONR^6R^7$; wherein $R^6$ and $R^7$ are as defined with respect to formula (I) above. Substituents most suitable for the aryl group include chloro, bromo, methoxy, $C_{1-6}$ alkyl, methoxycarbonyl, trifluoromethyl, nitro and —$NR^6R^7$.

Preferably the groups $R^2$, $R^{11}$ and/or $R^{12}$ independently represent hydrogen, halo, —$CF_3$, —$OR^6$, —$NR^6R^7$, —$NHNH_2$, —$CN$, —$COR^8$, phenyl($C_{1-3}$)alkyl $C_{3-6}$ cycloalkyl, adamantyl, $C_{2-6}$ alkenyl, $C_{2-6}$ alkynyl, $C_{1-6}$ alkyl, or $C_{1-6}$ alkyl substituted with —$OR^6$, —$NHR^6$, —$SR^6$, —$CO_2R^6$, —$CON(R^6)_2$ or halo; especially where $R^6$ and $R^7$ are each independently hydrogen or methyl. Particular values of the groups $R^2$, $R^{11}$ and/or $R^{12}$ are hydrogen hydroxy, chloro, methyl, ethyl, isopropyl, cyclopropyl, benzyl, adamantyl, amino, dimethylamino, methoxy, ethoxy, isopropoxy, n-butoxy, allyloxy, propargyloxy, methoxycarbonyl and ethoxycarbonyl. Preferred values are dimethylamino, methyl, methoxy, chloro and hydrogen, especially chloro.

A particularly preferred subgroup of formula (I) is wherein:

$R^1$ is a 7- or 8-membered azabicyclic ring system attached to the pyridine ring at the 3' carbon position of $R^1$;

$R^2$ is hydrogen, halo (especially chloro), —$OR^6$ (especially hydroxy, methoxy, or ethoxy), —$NR^6R^7$ (especially dimethylamino) or $C_{1-6}$ alkyl (especially methyl); and $R^{11}$ and $R^{12}$ are both hydrogen.

Especially preferred is when the azabicycle ($R^1$) is either unsubstituted or substituted at the 3'-position by hydrogen, halo (particularly chloro) or hydroxy, provided that, when $R^1$ is quinuclidine, then the substituent ($R^3$ or $R^4$) is other than 3'-hydroxy.

For example, compounds of formula (IA) or salts or prodrugs thereof:

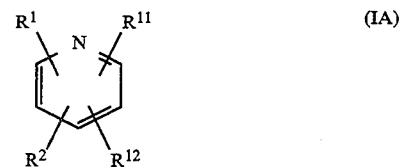

wherein
$R^1$ is selected from

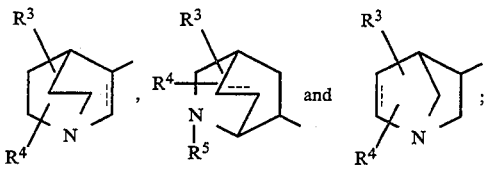

$R^2$, $R^{11}$ and $R^{12}$ are independently selected from hydrogen, halo, —$OR^6$, —$NR^6R^7$ and $C_{1-6}$alkyl; and $R^3$ and $R^4$ are independently selected from hydrogen, halo and hydroxy other than 3-hydroxy-3-(2-pyridyl)-1-azabicyclo[2.2.2]octane and 3-(2-pyridinyl)-1-azabicyclo[2.2.2]oct-2-ene.

Most of the compounds of this invention have at least one asymmetric centre and often more than one; and can therefore exist both as enantiomers and as diastereoisomers. In particular, those compounds possessing an unsymmetrical azabicyclic ring system may exist as exo and endo diastereoisomers. It is to be understood that the invention covers all such isomers and mixtures thereof.

One group of prodrugs of compounds of this invention have a substituent on the pyridine ring which is hydrolysable in vivo to an amino group.

Groups which are hydrolysable in vivo to an amino group in the compounds of this invention may be readily ascertained by administering the compound to a human or animal and detecting, by conventional analytical techniques, the presence of the corresponding compound having an amino substituent in the urine of the human or animal. Examples of such groups include, for example, amido and urethane substituents, in particular a group of formula —NH.Q, wherein Q represents CHO, COR or $CO_2R$, and R represents an optionally substituted hydrocarbon group.

In this context, the hydrocarbon group R includes groups having up to 20 carbon atoms, suitably up to 10 carbon atoms, conveniently up to 6 carbon atoms. Suitable groups R include $C_{1-9}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, and aryl($C_{1-6}$)alkyl. The alkyl group R may be straight or branched chain and may contain, for example, up to 12 carbon atoms, suitably from 1 to 6 carbon atoms. In particular the group may be substituted methyl, ethyl, n- or iso-propyl, n-, sec-, iso- or tert-butyl, n- or iso-heptyl, or n- or iso-octyl. Suitable cycloalkyl groups include cyclopentyl and cyclohexyl. The aryl group R includes phenyl and naphthyl optionally substituted with up to five, preferably up to three, substituent groups.

Also included within the scope of the present invention are salts of the novel compounds. It will be appreciated that salts of the compounds for use in medicine will be non-toxic pharmaceutically acceptable salts. Other salts may, however, be useful for the preparation of the compounds of the invention or their non-toxic pharmaceutically acceptable salts. Acid addition salts, for example, may be formed by mixing a solution of the compound with a solution of a pharmaceutically acceptable non-toxic acid such as hydrochloric acid, oxalic acid, fumaric acid, maleic acid, succinic acid, acetic acid, citric acid, tartaric acid, carbonic acid or phosphoric acid. Preferred acid addition salts are the dihydrogen chloride, sesquihydrogen chloride, hydrogen oxalate and dihydrogen oxalate. Where the compound carries a carboxylic acid group, the invention also contemplates salts thereof, preferably non-toxic, pharmaceutically acceptable salts thereof, such as the sodium, potassium and calcium salts thereof.

Salts of amine groups may also comprise the quaternary ammonium salts in which the amino nitrogen atom carries an alkyl, alkenyl, alkynyl or aralkyl group. Such quaternary ammonium derivatives penetrate poorly into the central nervous system and are therefore useful as peripherally selective muscarinic agents, useful for example as antispasmodic agents, agents to reduce gastric acid secretion, agents to block the muscarinic actions of acetylcholinesterase inhibitors in the treatment of myasthenia gravis and as agents to co-administer with muscarinic agonists in Alzheimer's disease.

Specific compounds within the scope of the present invention include the following:

3-[2-(6-chloropyridin)yl]-1-azabicyclo[2.2.2]octane;
3-[2-(6-dimethylaminopyridin)yl]-1-azabicyclo[2.2.2]octane;
3-[2-(6-methylpyridin)yl]-1-azabicyclo[2.2.2]octane;
3-[2-(6-methoxypyridin)yl]-1-azabicyclo[2.2.2]octane;
3-[3-(6-methoxypyridin)yl]-1-azabicyclo[2.2.2]octane;
3-(2-pyridinyl)-1-azabicyclo[2.2.2]octane;
3-(3-pyridinyl)-1-azabicyclo[2.2.2]octane;
3-(4-pyridinyl)-1-azabicyclo[2.2.2]octane;
6-[2-(6-methoxypyridin)yl]-2-azabicyclo[2.2.2]octane;
3-[2-(6-methoxypyridin)yl]-1-azabicyclo[2.2.1]heptane;
3-[2-(6hydroxypyridin)yl]-1-azabicyclo[2.2.2]octane;
3-chloro-3-(2-pyridinyl)-1-azabicyclo[2.2.2]octane;
3-hydroxy-3-(3-pyridinyl)-1-azabicyclo[2.2.2]octane;
3-(3-pyridinyl)-1-azabicyclo[2.2.2]oct-2-ene;
3-hydroxy-3-[3-(6-methoxypyridin)yl]-1-azabicyclo[2.2.2]octane;
3-[3-(6-methoxypyridin)yl)-1-azabicyclo[2.2.2]oct-2-ene;
3-hydroxy-3-[3-(5-methoxypyridin)yl]-1-azabicyclo[2.2.2]octane;
3-[3-(5-methoxypyridin)yl]-1-azabicyclo[2.2.2]oct-2-ene;
3-[3-(5-methoxypyridin)yl]-1-azabicyclo[2.2.2]octane;
3-hydroxy-3-[3-(5-ethoxypyridin)yl]-1-azabicyclo[2.2.2]octane;
3-[3-(5-ethoxypyridin)yl]-1-azabicyclo[2.2.2]oct-2-ene;
3-[3-(5-ethoxypyridin)yl]-1-azabicyclo[2.2.2]octane;
3-hydroxy-3-[2-(6-methylpyridin)yl]-1-azabicyclo[2.2.2]octane;
3-[2-(6-methylpyridin)yl]-1-azabicyclo[2.2.2]oct-2-ene;
3-hydroxy-3-[2-(6-ethoxypyridin)yl]-1-azabicyclo[2.2.2]octane;
3-[2-(6-ethoxypyridin)yl]-1-azabicyclo[2.2.2]oct-2-ene;
3-[2-(6-ethoxypyridin)yl]-1-azabicyclo[2.2.2]octane;
3-hydroxy-3-[3-(4-methylpyridin)yl]-1-azabicyclo[2.2.2]octane;
3-[3-(4-methylpyridin)yl]-1-azabicyclo[2.2.2]oct-2-ene;
3-[3-(4-methylpyridin)yl]-1-azabicyclo[2.2.2]octane;
3-hydroxy-3-[2-(6-methoxypyridin)yl]-1-azabicyclo[2.2.1]heptane;
3-[2-(6-methoxypyridin)yl]-1-azabicyclo[2.2.1]hept-2-ene;
2-benzyloxylcarbonyl-6-hydroxy-6-[2-(6-methoxypyridin)yl]-2-azabicyclo[2.2.2]octane;
2-benzyloxycarbonyl-6-chloro-6-[2-(6-methoxypyridin)yl]-2-azabicyclo[2.2.2]octane;
6-chloro-6-[2-(6-methoxypyridin)yl]-2-azabicyclo[2.2.2]octane;
6-[2-(6-methoxypyridin)yl]-2-azabicyclo[2.2.2]octane;
and salts and prodrugs thereof.

The method of treatment of this invention includes a method of treating Alzheimer's disease, senile dementia of the Alzheimer type, Huntington's chorea, tardive dyskinesia, hyperkinesia, mania or Tourette syndrome by the administration to a patient in need of such treatment of a non-toxic pharmacologically effective amount of a compound of formula (I), or a salt or prodrug thereof.

It may, where appropriate, be advantageous, in order to reduce unwanted peripherally mediated side-effects, to incorporate into any composition a peripherally acting cholinergic antagonist (or anti-muscarinic agent). Thus the compounds of the invention may be administered together with a peripheral cholinergic antagonist such as N-methylscopolamine, N-methylatropine, propantheline, methantheline or glycopyrrolate.

The compounds of the invention can be administered orally, parenterally or rectally at a daily dose of about 0.01 to 10 mg/kg of body weight, preferably about 0.1 to 1 mg/kg, and may be administered on a regimen of 1–4 times a day. When a cholinergic antagonist is administered, it is incorporated at its conventional dose.

The pharmaceutical formulations of this invention preferably are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic, pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills or capsules. This solid preformulation composition is then subdivided into unit dosage forms of the type described above containing from 0.1 to about 500 mg of the compound of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the compositions of the invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinylpyrrolidone and gelatin.

This invention also provides a pharmaceutical composition comprising a compound of the invention and a pharmaceutically acceptable carrier therefor.

The present invention further provides a process for preparing a pharmaceutical composition according to the invention, which process comprises bringing a compound of the invention into association with a carrier therefor, such as by mixing.

The present invention further provides a pharmaceutical composition comprising 3-(2-pyridinyl)-1-azabicyclo[2.2.2]oct-2-ene and a pharmaceutically acceptable carrier therefor; a process for preparing such a composition; and the use of this compound or a composition thereof in the treatment or prevention of neurodegenerative disorders.

The compounds of this invention wherein $R^3$ and $R^4$ are each other than hydroxy or carboxy substituted on the azacycle or azabicycle at the point of attachment to the pyridine ring may be prepared by a process which comprises the dehydroxylation or decarboxylation of a compound of formula (III) (which is a sub-class of the compounds of formula (I)) or a salt thereof:

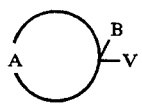
(III)

wherein V represents a pyridine ring, independently substituted on each of the remaining ring carbon atoms with a substituent of low lipophilicity or a hydrocarbon substituent; A represents the residue of an azacyclic or azabicyclic ring; and B represents hydroxy or a carboxy-containing group.

When the group B in compound (III) is hydroxy, it may be removed by chlorination and elimination, followed by hydrogenation. For example, chlorination and elimination may be effected by treatment with phosphorus oxychloride in the presence of triethylamine, or with thionyl chloride followed, where necessary, by DBN. The chloride or the unsaturated product may then be hydrogenated under conventional conditions, such as over 10% palladium/carbon in methanol. Alternatively, the compound (III) may be dehydroxylated by pyrolysis of the xanthate ester followed by hydrogenation. The xanthate ester may be formed by deprotonation of (III) with a metal hydride followed by quenching with carbon disulphide and subsequent alkylation. Alternatively, the compound (III) may be dehydroxylated by the use of thionyl chloride followed by treatment with tributyl tin hydride in a solvent such as tetrahydrofuran in the presence of a radical initiator such as azabisisobutyronitrile.

By analogy with the disclosure in J. Med. Chem. (1971), 14, 554–6, the compounds of formula (III) wherein B is hydroxy may be prepared by reaction of a ketone of formula (IV) with a metal derivative of a pyridine of formula (V):

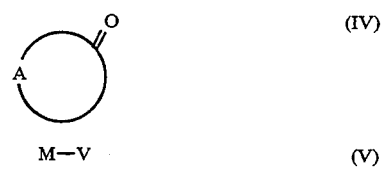

wherein A and V are as defined above; and M represents a metal atom, for example lithium. The metal derivative, for instance, may be prepared by reacting the corresponding halo-substituted pyridine such as iodo- or bromo-substituted pyrazine with t-butyl lithium, n-butyl lithium or the metal alone.

When the group B in compound (III) is carboxy, it may be removed by standard decarboxylation techniques such as by heating in aqueous solution made to pH1 with hydrochloric acid.

The compounds of formula (III) wherein B represents a carboxy-containing group may be prepared by reaction of a compound of formula (VI) with a compound of formula (VII):

wherein $R^1$ and V are as defined above, Hal represents halo (such as chloro, bromo or fluoro), and W represents cyano, a carboxylic acid group or a derivative thereof which activates the adjacent position such as an alkyl ester; and subsequently, where necessary, converting the group W to carboxy, preferably by hydrolysis.

Preferably, W represents an alkyl ester group such as methoxycarbonyl. Preferably, the halo group is chloro or fluoro. The reaction between compounds (VI) and (VII) may be carried out in the presence of a strong base such as lithium diisopropylamide (which may be prepared in situ from n-butyl lithium and diisopropylamine) in a solvent such as tetrahydrofuran.

The azacyclic or azabicyclic moiety may be introduced into the molecules concerned by methods known from the art, in particular by methods analogous to those described in EP-A-0239309.

After any of the above described processes is complete, one substituent can be converted to another. For example, an amino group may be converted to chloro, or hydrazo, —NHNH$_2$, via the intermediacy of diazonium (—N$_2$). Similarly, a chloro substituent may be converted to methoxy by reaction with a nucleophile such as methoxide, or to an alkyl group by reaction with a tetraalkyl stannane under palladium catalysis; alkoxycarbonyl groups may be converted, via carboxy, to an amino substituent (—NH$_2$); and methoxy may be converted to hydroxy by treatment with concentrated hydrobromic acid.

In any of the above reactions it may be necessary and/or desirable to protect any sensitive groups in the compounds. For example, if the reactants employed include amino, carboxy, keto, hydroxy or thiol groups, these may be protected in conventional manner. Thus, suitable protecting groups for hydroxy groups include silyl groups such as trimethylsilyl or t-butyl-dimethylsilyl, and etherifying groups such as tetrahydropyranyl; and for amino groups include benzyloxycarbonyl and t-butoxycarbonyl. Keto groups may be protected in the form of a ketal. Carboxy groups are oxycarbonyl and t-butoxycarbonyl. Keto groups may be protected in the form of a ketal. Carboxy groups are preferably protected in a reduced form such as in the form of their corresponding protected alcohols, which may be subsequently oxidised to give the desired carboxy group. Thiol groups may be protected by disulphide formation, either with the thiol itself or with another thiol to form a mixed disulphide. The protecting groups may be removed at any convenient stage in the synthesis of the desired compound according to conventional techniques.

The following Examples illustrate the preparation of compounds according to the invention. Each of the compounds of the Examples demonstrates an affinity for the muscarinic receptor, having an IC$_{50}$ (concentration required to displace 50% of specific [$^3$H]-N-methylscopolamine binding from rat cortical membrane preparations) significantly lower than 100 $\mu$M. Penetrability into the central nervous system of compounds of this invention was assessed by a measurable displacement of radioligand binding using standard "ex-vivo" binding techniques (Ref: *J. Neurosurg.*, 1985, 63, 589–592).

In the Examples, all temperatures are in °C.; THF is tetrahydrofuran; and ether is diethyl ether.

DESCRIPTION 1

3-Hydroxy-3-(2-pyridinyl)-1-azabicyclo[2.2.2]octane n-Butyl lithium (1.6M in hexanes, 17.4 ml, 27.9 mmol) was added dropwise to a solution of 2-bromopyridine (2.66 ml, 27.9 mmol) in ether (75 ml) cooled to −70° C. After 30 min a solution of 3-quinuclidinone (3.49 g, 27.9 mmol) in ether (25 ml) was added and the reaction mixture allowed to warm to −20° C. over 1 h. Methanol (50 ml) was added and the solution concentrated. The crude product was chromatographed through silica-gel using dichloromethane/methanol/ammonia (89:10:1) as eluent to give 1.58 g of the title compound as a tan solid. The dihydrochloride salt was prepared; m.p. 210°–5° C.; Found C, 51.82; H, 6.50; N, 9.98. C$_{12}$H$_{18}$N$_2$Cl$_2$O requires C, 51.99; H, 6.55; N, 10.10; $\delta$(360 MHz, D$_2$O) 8.792 (1H, d, J=5.4 Hz, py-H), 8.528 (1H, dt, J=8.1, 1.5 Hz, py-H), 8.139 (1H, d, J=8.1 Hz, py-H), 7.961 (1H, t, J=6.7 Hz, py-H), 4.177 (1H, d, J=14.3 Hz, H-2$_{ax}$), 3.661 (1H, d, J=14.3 Hz, H-2$_{eq}$), 3.54–3.35 (4H, m, H$_2$-6 and H$_2$-7) 2.55–1.65 (5H, m, H-4, H$_2$-5 and H$_2$-8); m/e 204 (M+).

EXAMPLE 1

3-[2-(6-Chloropyridin)yl]-1-azabicyclo[2.2.2]octane a. 3-Carbomethoxy-3-[2-(6-chloropyridin)yl]-1-azabicyclo[2.2.2]octane n-Butyl Lithium (1.6M in hexane, 34.5 ml, 55 mmol) was added to a solution of diisopropylamine (8.4 ml 60 mmol) in THF (400 ml) at 0° C. After 5 min, the solution was cooled to −40° C. and 3-carbomethoxy-1-azabicyclo[2.2.2]octane [C.A. Grob and E. Renk, Helv. Chim. Acta., (1954)37 1689](11.8 g, 69.6 mmol) in THF (50 ml) was added. The resulting solution was stirred at −40° C. for 1 h and then cooled to −78° C. 2,6-Dichloropyridine (7.45 g, 50 mmol) in THF (20 ml) was added and the mixture allowed to warm to room temperature. After 16 h, water (30 ml) was added and the mixture extracted with dichloromethane (3×100 ml). The combined extracts were dried over sodium sulphate and evaporated. The crude product was chromatographed through silica-gel using dichloromethane/methanol/ammonia (89:10:1) as eluent to give the 1.3g of the title compound as a yellow gum; $\delta$(250 MHz, CDCl$_3$), 7.63 (1H, t, J=7 Hz, py-H), 7.23 (2H, m, 2×py-H), 3.92 (1H, d, J=12 Hz, H-2), 3.78 (1H, d, J=12 Hz, H-2), 3.68–2.50 (6H, m, H-5, H$_2$-6, H$_2$-7, H-8), 1.80–1.40 (3H, m, H-4, H-5, H$_2$-6).

b. 3-[2-(6-Chloropyridin)yl]-1-azabicyclo[2.2.2]octane

A solution of the preceding ester (1.3 g, 4.6 mmol) in concentrated hydrochloric acid (15 ml) was heated at reflux for 3.5 h. The resulting mixture was concentrated, neutralised with sodium carbonate and then extracted with dichloromethane (3×20 ml). The combined organic extracts were dried over sodium sulphate, concentrated and the residue chromatographed through silica-gel using dichloromethane/methanol/ammonia (89:10:1) as eluent to give the title compound as a brown gum (0.32 g).

The hydrogen oxalate salt was prepared; m.p. 144°–7° C.; Found: C, 53.75; H, 5.55; N, 9.15. C$_{14}$H$_{17}$N$_2$ClO$_4$ requires C, 53.77; H, 5.48; N, 8.96; $\delta$(360 MHz, D$_2$O) 7.654 (1H, t, J=7.7 Hz, py-H), 7.268 (2H, d, J=7.7 Hz py-H), 7.147 (1H, d, J=7.7 Hz, py-H), 4.126 (1H, dd, J=5.7, 13.0 Hz, H-3), 3.64–3.20 (6H, m, H$_2$-2, H$_2$-6 and H$_2$-7) 2.38–1.60 (5H, m, H-4, H$_2$-5 and H$_2$-8); m/e 222 (M+)

EXAMPLE 2

3-[2-(6-Methoxypyridin)yl]-1-azabicyclo2.2.2]octane a. 3-Carbomethoxy-3-[2-(6-fluoropyridin)yl]-1-azabicyclo[2.2.2]octane n-Butyl lithium (1.6M in hexanes, 31.0 ml, 49.6 mmol) was added to a solution of diisopropylamine (6.95 ml, 49.6 mmol) in THF (75ml) at 0° C. and stirred for 5 min. The solution was cooled to −40° C. and 3-carbomethoxy-1-azabicyclo[2.2.2]octane (8.40 g, 49.6 mmol) in THF (75 ml) was added. The resulting solution was stirred at −40° C. for 1 h. A solution of 2,6-difluoropyridine (4.50 ml, 49.6 mmol) in THF (50 ml) was added and the resulting mixture warmed to room temperature and stirred for 16 h. Brine (200 ml) was added and the mixture extracted with ethyl acetate. The organic extract was dried over magnesium sulphate and concentrated. The crude product was chromatographed through silica-gel using dichloromethane/methanol/ammonia (89:10:1) as eluent to give 5.11 g of the title compound as a light yellow solid. The hydrochloride salt was prepared; m.p. 176°-8° C.; Found: C, 55.93; H, 6.06; N, 9.27. C$_{14}$H$_{19}$N$_2$ClFO$_2$ requires C, 55.72; H, 6.35; N, 9.28; δ(360 MHz, D$_2$O) 8.050 (1H, q, J=7.8 Hz, py-H), 7.570 (1H, dd, J=2.3, 7.8 Hz, py-H), 7.107 (1H, dd, J=2.3, 7.8 Hz, py-H), 4.332 (1H, dd, J=2.4, 13.7 Hz), 4.153 (1H, dd, J=2.0, 13.7 Hz), 3.719 (3H, s, OCH$_3$), 3.44–3.10 (5H, m, H-4, H$_2$-6, and H$_2$-7) 2.20–1.80 (4H, m, H$_2$-5 and H$_2$-8); m/e (CI+) 265 (M+1).

b. 3-Carbomethoxy-3-[2-(6-methoxypyridin)yl]-1-azabicyclo[2.2.2]octane and c. 3-[2-(6-Methoxypyridin)yl]-1-azabicyclo[2.2.2]octane 3-Carbomethoxy-3-[2-(6-fluoropyridin)yl]-1-azabicyclo[2.2.2]octane (0.43 g, 1.64 mmol, prepared as in Example 2a) was added to sodium (0.09 g, 3.9 mmol) in methanol (8 ml). The resulting solution was heated at reflux for 16 h, poured into brine (50 ml) and extracted with ethyl acetate. The organic extract was dried over magnesium sulphate and concentrated to give 3-carbomethoxy-3-[2-(6-methoxypyridin)yl]-1-azabicyclo[2.2.2]octane as yellow oil. This product was dissolved in concentrated hydrochloric acid (4 ml) and heated at reflux for 16 h, cooled and concentrated. The residue was dissolved in saturated aqueous potassium carbonate (50 ml) and extracted with dichloromethane. The organic extract was dried over magnesium sulphate, concentrated and then chromatographed through silica-gel with dichloromethane/methanol/ammonia (78:20:2) as eluent to give 0.13 g of the title compound as a light yellow oil. The dihydrochloride salt was prepared; m.p. 214°-6° C.; Found: C, 53.12; H, 7.01; N, 9.53. C$_{13}$H$_{20}$N$_2$Cl$_2$O. 0.15 H$_2$O requires C, 53.12; H, 6.96; N, 9.53; δ(360 MHz, d$_6$-DMSO) 7.521 (1H, dd, J=7.3 Hz, py-H), 6.780 (1H, d, J=7.3 Hz, py-H), 6.603 (1H, d, J=7.3 Hz, py-H), 4.04 (1H, m, H-3), 3.857 (3H, s, OCH$_3$) 3.50–3.10 (6H, m, H$_2$-2, H$_2$-6 and H$_2$-7) 2.24–1.60 (5H, m, H-4, H$_2$-5 and H$_2$-8); m/e 218 (M+).

EXAMPLE 3 a. 3-Carbomethoxy-3-[2-(6-dimethylaminopyridin)yl]-1azabicyclo[2.2.2]octane and b. 3-[2-(6-Dimethylaminopyridin)yl]-1-azabicyclo[2.2.2]octane A solution of 3-carbomethoxy-3-[2-(6-fluoropyridin)yl]-1-azabicyclo[2.2.2]octane (1.2 g, 4.54 mmol, prepared as in Example 2) in 40% aqueous dimethylamine (20 ml) was heated at reflux for 16 h. The reaction mixture was diluted with water and extracted with dichloromethane. The organic extract was dried over magnesium sulphate and concentrated. The residue was chromatographed through silica-gel with dichloromethane/methanol/ammonia (89:10:1) as eluent to give 0.23 g of 3-carbomethoxy-3-[2-(6-dimethylaminopyridin)yl]-1-azabicyclo[2.2.2]octane as a yellow oil. This product was dissolved in concentrated hydrochloric acid (6 ml) and the solution heated at reflux for 5 h, cooled and concentrated. The residue was dissolved in saturated aqueous potassium carbonate (50 ml) and extracted with dichloromethane. The organic extract was dried over magnesium sulphate, concentrated and chromatographed through silica-gel with dichloromethane/methanol/ammonia (89:10:1) as eluent to give 22 mg of the title compound as a yellow oil. The dihydrochloride salt was prepared; m.p. 140°-6° C.; δ(360 MHz, D$_2$O) 7.901 (1H, dd, J=7.4, 9.3 Hz, py-H), 7.077 (1H, d, J=9.3 Hz, py-H), 6.946 (1H, d, J=7.4 Hz, py-H), 4.10–3.60 (7H, m, H$_2$-2, H-3, H$_2$-6, H$_2$-7), 3.269 (6H, s, N(CH$_3$)$_2$), 2.53 (1H, m, H-4), 2.40–1.90 (4H, m, H$_2$-5, H$_2$-8); m/e 231 (M+).

EXAMPLE 4

3-[2-(6-Hydroxypyridin)yl]-1-azabicyclo[2.2.2]octane

3-Carbomethoxy-3-[2-(6-fluoropyridin)yl]-1-azabicyclo[2.2.2]octane (2.98 g, 11.3 mmol, prepared as in Example 2) was dissolved in concentrated hydrochloric acid (50 ml). The resulting solution was heated at reflux for 5.5 h, cooled to room temperature and concentrated. The residue was dissolved in saturated aqueous potassium carbonate (40 ml) and extracted with dichloromethane. The organic extract was dried over magnesium sulphate and concentrated to a white foam. The crude product was chromatographed through silica-gel using dichloromethane/methanol/ammonia (78:20:2) as eluent to give 0.19 g of the title compound as a hygroscopic white solid. The hydrogen oxalate salt was prepared; m.p. 35°–40° C.; Found: C, 53.96; H, 6.12; N, 8.45. C$_{12}$H$_{16}$N$_2$O. 1.4 (COOH)$_2$. 0.1 (C$_2$H$_5$)$_2$O requires C, 54.06; H, 5.91; N, 8.29; δ(360 MHz, D$_2$O) 7.723 (1H, dd, J=7.2, 9.0 Hz, py-H), 6.620 (1H, d, J=7.2 Hz, py-H), 6.561 (d, J=9.0 Hz, py-H), 3.72 (1H, m, H-3), 3.60–3.20 (4H, m, H$_2$-6 and H$_2$-7) 2.45–1.80 (5H, m, H-4, H$_2$-5 and H$_2$-8); m/e (CI+) 205 (M+1).

EXAMPLE 5

3-Chloro-3-(2-pyridinyl)-1-azabicyclo[2.2.2]octane

Thionyl chloride (0.74 ml, 10.2 mmol) was added dropwise to a solution of 3-hydroxy-3-(2-pyridinyl)-1-azabicyclo[2.2.2]octane (1.04 g, 5.09 mmol, prepared as in Description 1) in dichloromethane (10 ml). The reaction mixture was stirred at room temperature for 1 h, poured into saturated aqueous potassium carbonate (30 ml) and extracted with dichloromethane. The organic extract was dried over magnesium sulphate and then concentrated to a brown oil. The crude product was chromatographed through silica-gel using dichloromethane/methanol/ammonia (94.5:5:0.5) as eluent to give first 0.28 g of 3-chloro-3-(2-pyridinyl)-1-azabicyclo[2.2.2]octane followed by 0.39 g of 3-(2-pyridinyl)-1-azabicyclo[2.2.2]oct-2-ene.

The dihydrochloride salt of 3-chloro-3-(2-pyridinyl)-1-azabicyclo[2.2.2]octane was also prepared; m.p. 180°–195° C.; Found C, 48.29; H, 6.09; N, 8.98. C$_{12}$H$_{17}$N$_2$Cl$_{13}$. 0.25 H$_2$O requires C, 48.02; H, 5.88; N, 9.33; δ(360 MHz, D$_2$O) 8.641 (1H, d, J=4.3 Hz, py-H), 8.129 (1H, dt, J=1.8, 8.0 Hz, py-H), 7.897 (1H, d, J=8.0 Hz, py-H), 7.613 (1H, m, py-H), 4.780 (1H, dd, J=2.3, 14.7 Hz, H-2 $_{ax}$), 4.103 (1H, dd, J=2.4, 14.7 Hz, H-2$_{eq}$), 3.70–3.10 (4H, m, H$_2$-6 and H$_2$-7) 2.70 and 2.30–1.55 (5H, m, H-4, H$_2$-5 and H$_2$-8); m/e 222 (M+).

The dihydrochloride salt of 3-(2-pyridinyl)-1-azabicyclo[2.2.2]oct-2-ene was prepared; m.p. 215°–220° C.; Found: C, 55.57; H, 6.24; N, 10.68. C$_{12}$H$_{16}$N$_2$Cl$_2$ requires C, 55.61; H, 6.22; N, 10.81; δ(360 MHz, D$_2$O) 8.762 (1H, d, J=5.7 Hz, py-H), 8.543 (1H, t, J=8.0 Hz), 8.156 (1H, d, J=8.2 Hz, py-H), 7.989 (1H, t, J=6.4 Hz, py-H), 7.534 (1H, s, H-2), 3.80–3:30 (5H, m, H-4, H$_2$-6 and H$_2$-7) 2.24 and 1.97 (4H, m, H$_2$-5 and H$_2$-8); m/e 186 (M+).

EXAMPLE 6

3-(2-Pyridinyl)-1-azabicyclo[2.2.2]octane

A solution of 3-(2-pyridinyl)-1-azabicyclo[2.2.2]oct-2-ene dihydrochloride (0.28 g, prepared as in Example 5) in methanol (10 ml) was hydrogenated over 10% palladium on carbon (20 mg) in a Parr apparatus at 45 psi for 1 h. The suspension was filtered and concentrated. The crude product was recrystallised from methanol/ether to give 81 mg of the title compound as the dihydrochloride salt; m.p. 180°–190° C.; Found: C, 53.70; H, 7.04; N, 10.47. $C_{12}H_{18}N_2Cl_2 \cdot 0.35\ H_2O$ requires C, 53.88; H, 7.05; N, 10.47; $\delta$(360 MHz, $D_2O$) 8.738 (1H, d, J=5.6 Hz, py-H), 8.555 (1H, t, J=8.0 Hz, py-H), 8.086 (1H, d, J=8.2 Hz, py-H), 7.934 (1H, t, J=6.5 Hz, py-H), 4.00–3.75 (3H, m, $H_2$-2 and H-3), 3.60–3.30 (4H, m, $H_2$-6 and $H_2$-7) 2.54 (1H, m, H-4), 2.30–1.80 (4H, m, $H_2$-5 and $H_2$-8); m/e 188 (M+).

EXAMPLE 7

3-Hydroxy-3-( 3-:pyridinyl)-1-azabicyclo[2.2.2]octane

By the procedure described in Description 1, n-butyl lithium (1.6M in hexanes, 19.6 ml, 31.4 mmol), 3-bromopyridine (3.02 g, 31.4 mmol) and 3-quinuclidinone (3.93 g, 31.4 mmol) gave 3.62 g of the title compound as a light yellow solid. The dihydrochloride salt was prepared; m.p. 210°–220° C.; Found: C, 51.20; H, 6.51; N, 9.94. $C_{12}H_{18}N_2Cl_2O \cdot 0.25\ H_2O$ requires C, 51.17; H, 6.62; N, 9.94; $\delta$(360 MHz, $D_2O$) 8.993 (1H, s, py-H), 8.808 (1H, d, J=5.7 Hz, py-H), 8.741 (1H, d, J=7.8 Hz, py-H), 8.128 (1H, dd, J=5.7, 8.3 Hz, py-H), 3.960 (1H, d, J=14.1 Hz, H-$2_{ax}$), 3.722 (1H, dd, J=1.8, 14.1 Hz, H-$2_{eq}$), 3.45–3.30 (4H, m, $H_2$-6 and $H_2$-7), 2.70–1.60 (5H, m, H-4, $H_2$-5 and $H_2$-8); m/e 204 (M+).

EXAMPLE 8

3-( 3, Pyridinyl )-1-azabicyclo[2,2.2]oct-2-ene

By the procedure described in Example 5, thionyl chloride (2.26 ml, 31.0 mmol) and 3-hydroxy-3-(3-pyridinyl)-1-azabicyclo[2.2.2]octane (3.17 g, 15.5 mmol, prepared as in Example 7) gave 1.01 g of the title compound as a yellow oil. The dihydrochloride salt was prepared; m.p. 230°–2° C.; Found: C, 55.35; H, 6.17; N, 10.72. $C_{12}H_{16}N_2Cl_2$ requires C, 55.61; H, 6.22; N, 10.81; $\delta$(360 MHz, $D_2O$) 8.990 (1H, s, py-H), 8.802 (1H, d, J=5.6 Hz, py-H), 8.712 (1H, d, J=8.4 Hz, py-H), 8.103 (1H, dd, J=8.2, 5.8 Hz, py-H), 7.324 (1H, s, H-2), 3.69 and 3.26 (5H, m, H-4, $H_2$-6 and $H_2$-7), 2.21 and 1.95 (4H, m, $H_2$-5 and $H_2$-8); m/e 186 (M+).

EXAMPLE 9

3-(3,Pyridinyl)-1-azabicyclo[2.2.2]octane

By the procedure described in Example 6, hydrogenation of 3-(3-pyridinyl)-1-azabicyclo[2.2.2]oct-2-ene dihydrochloride (0.59 g, prepared as in Example 8) gave 0.49 g of the title compound as the dihydrochloride salt; m.p. 195°–205° C.; Found: C, 54.57; H, 6.96; N, 10.62. $C_{12}H_{18}N_2Cl_2 \cdot 0.15\ H_2O$ requires C, 54.62; H, 6.99; N, 10.62; $\delta$(360 MHz, $D_2O$) 8.824 (1H, s, py-H), 8.742 (1H, d, J=5.8 Hz, py-H), 8.633 (1H, d, J=8.2 Hz, py-H), 8.097 (1H, dd, J=5.8, 8.2 Hz, py-H), 4.00–3.30 (7H, m, $H_2$-2, H-3, $H_2$-6 and $H_2$-7) 2.50–1.80 (5H, m, H-4, $H_2$-5 and $H_2$-8); m/e 188 (M+).

EXAMPLE 10

3-(4-Pyridinyl), 1-azabicyclo[2.2.2]oct-2-ene a. 3-Hydroxy-3-(4-pyridinyl)-1-azabicyclo[2.2.2]octane By the procedure described in Description 1, n-butyl lithium (1.6M in hexanes, 19.5 ml, 31.2 mmol), 4-bromopyridine (5.37 g, 34.0 mmol) and 3-quinuclidinone (3.90 g, 31.2 mmol) gave 3.62 g of the title compound as a tan powder. The dihydrochloride salt was prepared; m.p. 225°–235° C.; Found: C, 50.50; H, 6.39; N, 9.76. $C_{12}G_{20}N_2$, $Cl_2O \cdot 0.5H_2O$ requires C, 50.36; H, 6.69; N, 9.79; $\delta$(360 MHz, $D_2O$) 8.854 (2H, d, J=6.8 Hz, py-H), 8.207 (2H, d, J=6.8 Hz, py-H), 4.016 (1H, d, J=14.2 Hz, H-$2_{ax}$), 3.696 (1H, d, J=14.2 Hz, H-$2_{eq}$), 3.52–3.30 (4H, m, $H_2$-6 and $H_2$-7), 2.70–1.60 (5H, m, H-4, $H_2$-5 and $H_2$-8); m/e 204 (M+).

b. 3-Chloro-3-(4-pyridinyl)-1-azabicyclo[2.2.2]octane and c. 3-(4-pyridinyl)1-azabicyclo[2.2.2]oct-2-ene By the procedure described in Example 5, thionyl chloride (2.38 ml, 32.7 mmol) and 3-hydroxy-3-(4-pyridinyl)-1-azabicyclo[2.2.2]octane (3.34 g, 15.4 mmol, prepared as in Example 10a) gave 0.11 g of 3-chloro-3-(4-pyridinyl)-1-azabicyclo[2.2.2]octane dihydrochloride; m.p. 165°–170° C.; Found: C, 46.78; H, 5.97; N, 8.77. $C_{12}H_{17}N_2Cl_3 \cdot 0.75H_2O$ requires C, 46.62; H, 6.03; N, 9.06; $\delta$(360 MHz, $D_2O$) 8.882 (2H, d, J= 7.0 Hz, py-H), 8.231 (2H, d, J=7.9 Hz, py-H), 4.38 (2H, m, H$_2$-2), 3.70–3.15 (4H, m, H$_2$-6 and H$_2$-7), 2.75–1.60 (5H, m, H-4, H$_2$-5 and H$_2$-8); m/e 222 (M+), and 1.29 g of 3-(4-pyridinyl)-1-azabicyclo[2.2.2]oct-2-ene dihydrochloride; m.p. 245°–250° C.; Found: C, 55.40; H, 6.19; N, 10.68. $C_{12}H_{16}N_2Cl_2 \cdot 0.05H_2O$ requires C, 55.41; H, 6.24; N, 10.77; $\delta$(360 MHz, $D_2O$) 8.814 (2H, d, J=6.9 Hz, py-H), 8.171 (2H, d, J=6.9 Hz, py-H), 7.529 (1H, d, J=1.4 Hz, H-2), 3.73 and 3.27 (5H, m, H-4, H$_2$-6 and H$_2$-7), 2.25 and 1.93 (4H, m, H$_2$-5 and H$_2$-8); m/e 186 (M+).

EXAMPLE 11

3-(4-Pyridinyl)-1-azabicyclo[2.2.2]octane

By the procedure described in Example 6, hydrogenation of 3-(4-pyridinyl)-1-azabicyclo[2.2.2]oct-2-ene dihydrochloride (1.07 g, prepared as in Example 10c) gave 0.75 g of the title compound as the dihydrochloride salt; m.p. 210°–220° C.; Found: C, 54.18; H, 6.93; N, 10.54. $C_{12}H_{18}N_2Cl_2 \cdot 0.25H_2O$ requires C, 54.25; H, 7.02; N, 10.54; $\delta$(360 MHz, $D_2O$) 8.772 (2H, d, J=6.8 Hz, py-H), 8.063 (2H, m, J=6.8 Hz, py-H), 4.00–3.30 (6H, m, H$_2$-2, H$_2$-6 and H$_2$-7) 2.60–1.85 (5H, m, H-4, H$_2$-5 and H$_2$-8); m/e 188 (M+).

EXAMPLE 12

3-Hydroxy-3-[3-(6-methoxypyridin)yl]-1-azabicyclo[2.2.2]octane

By the procedure described in Description 1, n-butyl lithium (1.6M in hexanes, 18.7 ml, 30.0 mmol), 2-methoxy-5-bromopyridine [L. Testaferri et al, Tetrahedron, (1985) 41 1373–1384] (5.63 g, 30.0 mmol) and 3-quinuclidinone (3.75 g, 30.0 mmol) gave 4.72 g of the title compound as a cream powder. The hydrogen oxalate salt was prepared; m.p. 214°–8° C.; Found: C, 59.30; H, 6.70; N, 9.86. $C_{14}H_{19}N_2O_4 \cdot 0.25H_2O$ requires C, 59.25; H, 6.93; N, 9.87; $\delta$(360 MHz, $D_2O$) 8.334 (1H, d, J=2.7 Hz py-H), 7.930 (1H, dd, J=2.7, 8.9 Hz, py-H), 6.984 (1H, d, J=8.9 Hz, py-H), 3.947 (1H, d, J=13.9 Hz, H-$2_{ax}$), 3.939 (3H, s, OCH$_3$), 3.608 (1H, dd, J=2.1, 13.9 Hz, H-$2_{eq}$), 3.50–3.22 (4H, m, H$_2$-6 and H$_2$-7) 2.70–1.65 (5H, m, H-4, H$_2$-5 and H$_2$-8); m/e 234 (M+).

EXAMPLE 13

3-[3-(6-Methoxypyridin)yl]-1-azabicyclo[2.2.2]oct-2-ene

By the procedure described in Example 5, thionyl chloride (2.45 ml, 33.6 mmol) and 3-hydroxy-3-[3-(6-methoxypyridin)yl]-1-azabicyclo[2.2.2]octane (3.95 g, 16.8 mmol, prepared as in Example 12) gave 1.35 g of the title compound as a yellow oil. The dihydrochloride salt was prepared; m.p. 237°-243° C.; Found: C, 54.69; H, 6.37; N, 9.90. $C_{13}H_{16}N_2O.1.9HCl$ requires C, 54.68; H, 6.32; N, 9.81; $\delta$(360 MHz, $D_2O$) 8.429 (1H, d, J=2.4 Hz, py-H), 8.347 (1H, dd, J=2.4, 9.0 Hz, py-H), 7.350 (1H, d, J=9.0 Hz, py-H), 7.106 (1H, s, H-2), 4.133 (3H, s, $OCH_3$), 3.65 and 3.23 (5H, m, H-4, $H_2$-6 and $H_2$-7), 2.19 and 1.91 (4H, m, $H_2$-5 and $H_2$-8); m/e 216 ($M^+$).

EXAMPLE 14

3-[3-(6-Methoxypyridin)yl]-1-azabicyclo[2.2.2]octane

By the procedure described in Example 6, hydrogenation of 3-[3-(6-methoxypyridin)yl]-1-azabicyclo[2.2.2]oct-2-ene dihydrochloride (1.21 g, prepared as in Example 13) gave 0.58 g of the title compound as the sesquihydrochloride salt; m.p. 170°-5° C.; Found: C, 57.16; H, 7.12; N, 10.33. $C_{13}H_{18}N_2O.1.5HCl$ requires C, 57.20; H, 7.20; N, 10.26; $\delta$(360 MHz, $D_2O$) 8.133 (1H, d, J=2.5 Hz, py-H), 7.945 (1H, dd, J=2.5, 8.8 Hz, py-H), 7.078 (1H, d, J=8.8 Hz, py-H), 3.985 (3H, s, $OCH_3$), 3.82 (1H, m, H-3), 3.60-3.30 (6H, m, $H_2$-2, $H_2$-6 and $H_2$-7) 2.34-1.80 (5H, m, H-4, $H_2$-5 and $H_2$-8): m/e 218 ($M^+$).

EXAMPLE 15

3-Hydroxy-3-[3-(5-methoxypyridin)yl]-1-azabicyclo[2.2.2]octane

By the procedure described in Description 1, n-butyl lithium (1.6M in hexanes, 21.9 ml, 35.1 mmol), 3-bromo-5-methoxypyridine [prepared from 3,5-dibromopyridine and sodium methoxide, L. Testaferri et al, Tetrahedron (1985) 41 1373-1384](6.60 g, 35.1 mmol) and 3-quinuclidinone (4.39 g, 35.1 mmol) gave 2.90 g of the title compound as a white powder; m.p. 133°-5° C.; Found: C, 66.76; H, 7.80; N, 11.92. $C_{13}H_{18}N_2O_2$ requires C, 66.64; H, 7.74; N, 11.96; $\delta$(360 MHz, $CDCl_3$) 8.311 (1H, s, py-H), 8.183 (1H, d, J=2.7 Hz, py-H), 7.350 (1H, t, J=2.7 Hz, py-H), 3.874 (3H, s, $OCH_3$), 3.417 (1H, dd, J=1.8, 14.5 Hz, $H-2_{ax}$) 3.052 (1H, d, J=14.5 Hz, $H-2_{eq}$), 3.04-2.75 (5H, m, OH, $H_2$-6 and $H_2$-7) 2.25-1.30 (5H, m, H-4, $H_2$-5 and $H_2$-8); m/e 234 ($M^+$).

EXAMPLE 16

3-[3-(5-Methoxypyridin)yl]-1-azabicyclo[2.2.2]oct-2-ene

By the procedure described in Example 5, thionyl chloride (1.66 ml, 22.8 mmol) and 3-hydroxy-3-[3-(5-methoxypyridin)yl]-1-azabicyclo[2.2.2]octane (2.67 g, 1.4 mmol, prepared as in Example 15) gave 1.13 g of the title compound as a yellow oil. The dihydrochloride salt was prepared; m.p. 200°-210° C.; Found: C, 42.89; H, 6.61; N, 9.11. $C_{13}H_{18}N_2Cl_2O.0.4H_2O$ requires C, 52.68; H, 6.39; N, 9.45; $\delta$(360 MHz, $D_2O$) 8.606 (1H, s, py-H), 8.521 (1H, d, J=2.5 Hz, py-H), 8.211 (1H, t, J=2.5 Hz, py-H), 7.316 (1H, s, H-2), 4.067 (3H, s, $OCH_3$), 3.71 and 3.29 (5H, m, H-4, $H_2$-6 and $H_2$-7), 2.23 and 1.94 (4H, m, $H_2$-5 and $H_2$-8); m/e 216 ($M^+$).

EXAMPLE 17

3-[3-(5-Methoxypyridin)yl]-1-azabicyclo[2.2.2]octane

By the procedure described in Example 6, hydrogenation of 3-[3-(5-methoxypyridin)yl]-1-azabicyclo[2.2.2]oct-2-ene dihydrochloride (1.31 g, prepared as in Example 16) gave 0.45 g of the title compound as the dihydrochloride salt; m.p. 201°-3° C.; Found: C, 50.20; H, 7.14; N, 9.00. $C_{13}H_{20}N_2Cl_2O.1.1H_2O$ requires C, 50.20; H, 7.19; N, 9.01; $\delta$(360 MHz, $D_2O$) 8.450 (1H, s, py-H), 8.443 (1H, S, py-H), 8.119 (1H, t, J=1.9 Hz, py-H), 4.044 (3H, s, $OCH_3$), 3.93 (1H, m, $H-2_{ax}$), 3.81 (1H, m, $H-2_{eq}$), 3.62 (1H, m, H-3), 3.44 (4H, m, $H_2$-6 and $H_2$-7), 2.50-1.85 (5H, m, H-4, $H_2$-5 and $H_2$-8); m/e ($CI^+$) 219 (M+1).

EXAMPLE 18

3-Hydroxy-3-[3-(5-Ethoxypyridin)yl]-1-azabicyclo[2.2.2]octane

By the procedure described in Description 1, n-butyllithium (1.6M in hexanes, 19.3 ml, 30.9 mmol), 3-bromo-5-ethoxypyridine [prepared from 3,5-dibromopyridine and sodium ethoxide, L. Testaferri et al, Tetrahedron (1985) 41 1373-1384] (6.25 g, 30.9 mmol) and 3-quinuclidinone (3.87 g, 30.9 mmol) gave 3.81 g of the title compound as a white solid; m.p. 160°-3° C.; Found: C, 67.61; H, 8.12; N, 11.15. $C_{14}H_{20}N_2O_2$ requires C, 67.72; H, 8.11; N, 11.28; $\delta$(360 MHz, $CDCl_3$) 8.282 (1H, d, J=1.8 Hz, py-H), 8.151 (1H, d, J=2.7 Hz, py-H), 7.329 (1H, dd, J=1.8, 2.7 Hz, py-H), 4.092 (2H, q, J=7.0 Hz, $CH_2$ of $OCH_2CH_3$), 3.395 (1H, dd, J=1.1, 14.5 Hz, $H-2_{ax}$), 3.18 (1H, br, OH), 3.034 (1H, d, J=14.5 Hz, $H=2_{eq}$), 3.04-2.64 (4H, m, $H_2$-6 and $H_2$-7), 2.25-1.45 (5H, m, H-4, $H_2$-5 and $H_2$-8), 1.440 (3H, t, J=7.0 Hz, $CH_3$ of $OCH_2CH_3$); m/e 248 ($M^+$).

EXAMPLE 19

3-[3-(5-Ethoxypyridin)yl]-1-azabicyclo[2.2.2]oct-2-ene

By the procedure described in Example 5, thionyl chloride (2.05 ml, 28.1 mmol) and 3-hydroxy-3-[3-(5-ethoxypyridin)yl]-1-azabicyclo[2.2.2]octane (3.49 g, 14.1 mmol, prepared in Example 18) gave 2.03 g of the title compound as a yellow oil. The dihydrochloride salt was prepared; m.p. 190°-7° C.; Found: C, 53.28; H, 6.81; N, 8.87. $C_{14}H_{20}N_2Cl_2O.0.7H_2O$ requires C, 53.24; H, 6.83; N, 8.87; $\delta$(360 MHz, $D_2O$) 8.587 (1H, d, J=1.2 Hz, py-H), 8.492 (1H, d, J=2.5 Hz, py-H), 8.175 (1H, t, J=2.1 Hz, py-H), 7.309 (1H, d, J=1.5 Hz, H-2), 4.345 (2H, q, J=7.0 Hz, $CH_3$ of $OCH_2CH_3$), 3.72 and 3.26 (5H, m, H-4, $H_2$-6 and $\overline{H}_2$-7), 2.26 and 1.94 (4H, m, $H_2$-5 and $H_2$-8), 1.476 (3H, t, J=7.0 Hz, $C\underline{H}_3$ of $OCH_2CH_3$): m/e 230 ($M^+$).

EXAMPLE 20

3-[3-(5-Ethoxypyridin)yl]-1-azabicyclo[2.2.2]octane

By the procedure described in Example 6, hydrogenation of 3-[3-(5-ethoxypyridin)yl]-1-azabicyclo[2.2.2]oct-2-ene dihydrochloride (2.02 g, prepared as in Example 19) gave 0.95 g of the title compound as the dihydrochloride salt; m.p. 182°-5° C.; Found: C, 54.31; H, 7.15; N, 9.02. $C_{14}H_{22}N_2Cl_2O.0.25H_2O$ requires C, 54.29; H, 7.32; N, 9.04; $\delta$(360 MHz, $D_2O$) 8.414 (2H, s, py-H), 8.070 (1H, s, py-H), 4.310 (2H, q, J=7.0 Hz, $CH_2$ of $OCH_2CH_3$), 3.90 (1H, m, $H-2_{ax}$), 3.81 (1H, m, $H-2_{eq}$), 3.61 (1H, m, H-3), 3.43 (4H, m, $H_2$-6 and $H_2$-7), 2.45 (1H, m, H-4), 2.17 and 1.87 (4H, m, $H_2$-5 and $H_2$-8), 1.451 (3H, t, J=7.0 Hz, CH$_3$ of OCH$_2$CH$_3$); m/e (CI+) 233 (M+1).

EXAMPLE 21

3-Hydroxy-3-[2-(6-methylpyridin)yl]-1-azabicyclo[2.2.2]octane

By the procedure described in Description 1, n-butyl lithium (1.6M in hexanes, 25.6 ml, 40.9 mmol), 2-bromo-6-methyl pyridine [N. Furukawa et al, J. C. S. Perkin I (1984) 1839–1845](7.04 g, 40.9 mmol) and 3-quinuclidinone (6.0 g, 47.9 mmol) gave 3.34 g of the title compound as a white solid; m.p. 150° C. dec; δ(360 MHz, CDCl$_3$) 7.78 (1H, t, J=9.7 Hz, py-H), 7.64 (1H, d, J=7.8 Hz, py-H), 7.19 (1H, d, J=7.8 Hz, py-H), 4.77 (2H, m, H$_2$-2), 3.36 (4H, m, H$_2$-6 and H$_2$-7), 2.55 (3H, s, py-CH$_3$), 2.60–1.50 (6H, m, OH, H-4, H$_2$-5 and H$_2$-8); m/e 218 (M+).

EXAMPLE 22

3-[2-(6-Methylpyridin)yl]-1-azabicyclo[2.2.2]oct-2-ene

By the procedure described in Example 5, thionyl chloride (2.0 ml, 27 mmol) and 3-hydroxy-3-[2-(6-methylpyridin)yl]-1-azabicyclo[2.2.2]octane (1.98 g, 9.1 mmol, prepared as in Example 21) gave 0.69 g of the title compound as a yellow oil. The dihydrochloride salt was prepared; m.p. 206°–8° C.; Found: C, 56.06; H, 6.60; N, 9.98. C$_{13}$H$_{18}$N$_2$Cl$_2$. 0.25H$_2$O requires C, 56.22; H, 6.71; N, 10.09; δ(360 MHz, D$_2$O) 7.65 (1H, t, J=8 Hz, py-H), 7.26 (1H, d, J=8 Hz, py-H), 7.08 (1H, d, J=8 Hz, py-H), 6.83 (1H, s, H-2), 2.99 and 2.51 (5H, m, H-4, H$_2$-6 and H$_2$-7), 2.09 (3H, s, py-CH$_3$), 1.47 and 1.20 (4H, m, H$_2$-5 and H$_2$-8); m/e 200 (M+).

EXAMPLE 23

3-[2-(6-Methylpyridin)yl]-1-azabicyclo[2.2.2]octane

By the procedure described in Example 6, hydrogenation of 3-[2-(6-methylpyridin)yl]-1-azabicyclo[2.2.2]oct-2-ene dihydrochloride (0.69 g, prepared as in Example 21) gave 0.55 g of the title compound free base as a cream solid. The hydrogen oxalate salt was prepared; m.p. 143°–4° C.; Found: C, 60.69; H, 6.83; N, 9.38. C$_{13}$H$_{18}$N$_2$. 1.1 (COOH)$_2$ requires C, 60.59; H, 6.76; N, 9.30; δ(360 MHz, D$_2$O) 8.22 (1H, t, J=8 Hz, py-H), 7.72 (1H, d, J=8 Hz, py-H), 7.60 (1H, d, J=8 Hz, py-H), 3.82 and 3.44 (7H, m, H$_2$-2, H-3, H$_2$-6 and H$_2$-7), 2.70 (3H, s, py-CH$_3$), 2.47 (1H, m, H-4), 2.17 and 1.86 (4H, m, H$_2$-5 and H$_2$-8); m/e 202 (M+).

EXAMPLE 24

3-Hydroxy-3-[2-(6-ethoxypyridin)yl]-1-azabicyclo[2.2.2]octane

By the procedure described in Description 1, t-butyl lithium (1.7M in pentane, 26.5 ml, 45.0 mmol), 2-bromo-6-ethoxypyridine [prepared from 2,6-dibromopyridine and sodium ethoxide, L. Testaferri et al, Tetrahedron (1985) 41 1373–1384] (4.52 g, 22.3 mmol) and 3-quinuclidinone (3.3 g, 26.4 mmol) gave 4.53 g of the title compound as a white solid; m.p. 127°–9° C.; δ(360 MHz, CDCl$_3$) 7.66 (1H, t, J=8.2 Hz, py-H), 7.28 (1H, d, J=8.9 Hz, py-H), 6.70 (d, J=8.2 Hz, py-H), 4.35 (4H, m, H$_2$-2 and CH$_2$ of OCH$_2$CH$_3$), 3.40 (4H, m, H$_2$-6 and H$_2$-7), 2.70 (1H, m, H-4), 2.28 (OH), 1.80 (4H, m, H$_2$-5 and H$_2$-8), 1.40 (3H, t, J=7 Hz, CHH$_3$ of OCH$_2$CH$_3$); m/e 248 (M+).

EXAMPLE 25

3-[2-(6-Ethoxypyridin)yl]-1-azabicyclo[2.2.2]oct-2-ene

By the procedure described in Example 5, thionyl chloride (2.48 ml, 34.1 mmol) and 3-hydroxy-3-[2-(6-ethoxypyridin)yl]-1-azabicyclo[2.2.2]octane (4.23 g, 17.0 mmol, prepared as in Example 24) gave 1.05 g of the title compound as a yellow oil. The hydrogen oxalate salt was prepared; m.p. 112°–4° C.; Found: C, 58.79; H, 6.27; N, 8.46. C$_{14}$H$_{18}$N$_2$O. (COOH)$_2$.0.4H$_2$O requires C, 58.67; H, 6.40; N, 8.55. δ(360 MHz, D$_2$O) 7.84 (1H, dd, J=7.4 and 8.4 Hz, py-H), 7.32 (1H, d, J=7.4 Hz, py-H), 7.28 (1H, s, H-2), 6.91 (1H, d, J=8.4 Hz, py-H), 4.37 (2H, q, J=7.0 Hz, CH$_2$ of OCH$_2$CH$_3$), 3.82, 3.61 and 3.19 (5H, m, H-4, H$_2$-6 and H$_2$-7), 2.16 and 1.84 (4H, m, H$_2$-5 and H$_2$-8), 1.39 (3H, t, J =7.0 Hz, CH$_3$ of OCH$_2$CH$_3$); m/e 230 (M+).

EXAMPLE 26

3-[2-(6-Ethoxypyridin)yl]-1-azabicyclo[2.2.2]octane

By the procedure described in Example 6, hydrogenation of the dihydrochloride salt of 3-[2-(6-ethoxypyridin)yl]-1-azabicyclo[2.2.2]-oct-2-ene (1.18 g, prepared as in Example 25) gave 0.29 g of the title compound free base as a pale yellow oil. The hydrogen oxalate salt was prepared; m.p. 162.5°–164° C.; Found: C, 59.45; H, 6.86; N, 8.69. C$_{14}$H$_{20}$N$_2$O. (COOH)$_2$ requires C, 59.62; H, 6.88; N, 8.69; δ(360 MHz, D$_2$O) 7.78 (1H, dd, J=7.4 and 8.3 Hz, py-H), 7.04 (1H, d, J=7.4 Hz, py-H), 6.78 (1H, d, J=8.3 Hz, py-H), 4.37 (2H, m, CH$_2$ of OCH$_2$CH$_3$), 4.02 (1H, m, H-3), 3.63–3.78 (6H, m, H$_2$-2, H$_6$ and H$_2$-7), 2.35 (1H, m, H-4), 2.13 and 1.81 (4H, m, H$_2$-5 and H$_2$-8), 1.40 (3H, t, J=7 Hz, CH$_3$ of OCH$_2$CH$_3$); m/e 232 (M+).

EXAMPLE 27

3-Hydroxy-3-[3-(4-methylpyridin)yl]1-azabicyclo[2.2.2]octane

By the procedure described in Description 1, t-butyl lithium (1.7M in pentane, 8.15 ml, 13.8 mmol), 3-bromo-4-methylpyridine [D. L. Comins et al, Heterocycles (1984) 22 339–344] (1.19 g, 6.9 mmol) and 3-quinuclidinone (0.88 g, 7.0 mmol) gave 0.45 g of the title compound as a white solid; m.p. 173.5°–174.5° C.; Found: C, 71.17; H, 8.28; N, 12.67. C$_{13}$H$_{18}$N$_2$O requires C, 71.53; H, 8.31; N, 12.83; δ(360 MHz, CDCl$_3$) 8.40 (1H, s, py-H), 8.30 (1H, d, J=4.9 Hz, py-H), 7.11 (1H, d, J=4.9 Hz, py-H), 3.37 and 3.06 (2H, m, H$_2$-2), 2.81 (4H, m, H$_2$-6 and H$_2$-7), 2.53 (3H, s, py-CH$_3$), 2.49 (1H, m, H-4), 2.25–1.50 (5H, m, OH, H$_2$-5 and H$_2$-8); m/e 218 (M+).

EXAMPLE 28

3-[3-(4-methylpyridin)yl]1-azabicyclo[2.2.2]oct-2-ene

By the procedure described in Example 5, thionyl chloride (6.2 ml, 82.5 mmol) and 3-hydroxy-3-[3-(4-methylpyridin)yl]-1-azabicyclo[2.2.2]octane (6.0 g, 27.5 mmol, prepared as in Example 27), gave 0.4ling of the title compound as a yellow oil. The di(hydrogen oxalate) salt was prepared; m.p. 185°–6° C.; Found: C, 53.59; H, 5.31; N, 7.33. C$_{13}$H$_{16}$N$_2$. 2(COOH)$_2$ requires C, 53.68; H, 5.30; N, 7.37; δ(360 MHz, D$_2$O) 8.64 (1H, d, J=6 Hz, py-H), 8.62 (1H, s, H-2), 7.97 (1H, d, J=6 Hz, py-H), 7.04 (1H, s, py-H), 3.71 and 3.31 (4H, m, H$_2$-6 and H$_2$-7), 3.39 (1H, m, H-4), 2.67 (3H, s, py-CH$_3$), 2.22 and 2.02 (4H, m, H$_2$-5 and H$_2$-8); m/e 200 (M+).

EXAMPLE 29

3-[3-(4-methylpyridin)yl]-1-azabicyclo[2.2.2]]octane

By the procedure described in Example 6, hydrogenation of 3-[3-(4-methylpyridin)yl]-1-azabicyclo[2.2.2]oct-2-ene di(hydrogen oxalate) (0.14 g, prepared as in Example 28) gave 0.10 g of the title compound free base as a yellow oil. The di(hydrogen oxalate) salt was prepared; m.p. 118.5°–120° C.; Found: C, 50.99; H, 6.08; N, 6.77. $C_{13}H_{18}N_2$. $2(COOH)_2$. $H_2O$ requires C, 51.00; H, 6.04; N, 7.00; δ(360 MHz, $D_2O$) 8.72 (1H, s, py-H), 8.58 (1H, d, J=6 Hz, py-H), 7.93 (1H, d, J=6 Hz, py-H), 3.88 and 3.46 (7H, m, $H_2$-2, H-3, $H_2$-6 and $H_2$-7), 2.66 (3H, s, py-$CH_3$), 2.24 and 1.93 (5H, m, H-4, $H_2$-5 and $H_2$-8); m/e 2-2 (M+).

EXAMPLE 30

3-Hydroxy-3-[2-(6-methoxypyridin)yl]-1-azabicyclo[2.2.1]heptane t-Butyllithium (1.7M in pentane, 54.5 ml, 92.6 mmol) was added dropwise to a solution of 2-bromo-6-methoxypyridine [L. Testaferri et al, Tetrahedron (1985) 41 1373–1384] (8.7 g, 46.3 mmol) in ether (250 ml) cooled to −70° C. After 1 h, a solution of 1-azabicyclo[2.2.1]heptan-3-one [J. Saunders et al, J. C. S. Chem. Commun., (1988) 1618–1619] (4.29 g, 38.6 mmol) in ether (150 ml) was added and the mixture allowed to warm to −20° C. over. 1 h. The reaction was quenched with MeOH (50 ml) and concentrated. The residue was purified by chromatography through silica-gel using dichloromethane/methanol/ammonia (89:10:1) as eluent to give 7.85 g of the title compound as a white solid; m.p. 209°–210° C.; δ(360 MHz, $CDCl_3$) 7.67 (1H, t, J=7 Hz, py-H), 7.33 (1H, d, J=7 Hz, py-H), 6.71 (1H, d, J=7 Hz, py-H), 4.40 (1H, dd, J=2, 12 Hz, H-2), 4.07 (1H, d, J=12 Hz, H-2), 3.94 (3H, s, $OCH_3$), 3.64–3.10 (5H, m, OH, $H_2$-6 and $H_2$-7), 2.96 (1H, d, J=4 Hz, H-4), 2.73 (1H, m, H-5), 2.00 (1H, m, H-5); m/e 220 (M+).

EXAMPLE 31

3-[2-(6-Methoxypyridin)yl]-1-azabicyclo[2.2.1]hept-2-ene

By the procedure described in Example 5, thionyl chloride (9.11 ml, 0.12mol) and 3-hydroxy-3-[2-(6-methoxypyridin)yl]-1-azabicyclo[2.2.1]heptane (6.67 g, 30.3 mmol, prepared as in Example 30) gave 2.65 g of the title compound as a yellow oil. The hydrogen oxalate salt was prepared; m.p. 123.5°–125° C.; Found: C, 57.22; H, 5.76; N, 9.73. $C_{12}H_{14}N_2O$. $(COOH)_2$ requires C, 57.53; H, 5.52; N, 9.58; δ(360 MHz $D_2O$) 7.84 (1H, dd, J=7, 8 Hz, py-H), 7.28 (1H, d, J=7 Hz, py-H), 7.21 (1H, s, H-2), 6.93 (1H, d, J=8 Hz, py-H), 4.18–3.22 (5H, m, H-4, $H_2$-6 and $H_2$-7), 3.95 (3H, s, $OCH_3$), 2.47 (1H, m, H-5), 1.79 (1H, m, H-5); m/e 202 (M+).

EXAMPLE 32

(a) Exo-3-[2-(6-methoxypyridin)yl]-1-azabicyclo[2.2.1]heptane and (b) endo-3-[2(6methoxypyridin)yl]-1-azabicyclo[2.2.1]heptane By the procedure described in Example 6, hydrogenation of 3-[2-(6-methoxypyridin)yl]-1-azabicyclo[2.2.1]hept-2-ene (2.1 g, prepared as in Example 31) gave a 1:4 mixture of the title compounds. Separation of the mixture by chromatography through silica-gel using dichloromethane/methanol/ammonia (89:10:1) as eluent gave 0.23 g of the exo-isomer followed by 1.00 g of the endo-isomer.

The hydrogen oxalate salt of exo-3-[2-(6-methoxypyridin)yl]-1-azabicyclo[2.2.1]heptane was prepared; m.p. 134°–5° C.; Found: C, 57.08; H, 6.44; N, 9.59. $C_2H_{16}N_2O$. $(COOH)_2$ requires C, 57.14; H, 6.17; N, 9.52; δ(360 MHz, $D_2O$) 7.74 (1H, dd, J=7,8 Hz, py-H), 7.02 (1H, d, J=7 Hz, py-H), 6.79 (1H, d, J=8 Hz, py-H), 4.00–3.06 (7H, m, $H_2$-2, H-4, $H_2$-6 and $H_2$-7), 3.94 (3H, s, $OCH_3$), 2.21 (1H, m, H-5), 1.93 (1H, m, H-5); m/e 204 (M+).

The hydrogen oxalate salt of endo-3-[2-(6-methoxypyridin)yl]-1-azabicyclo[2.2.1]heptane was prepared; m.p. 126°–127° C.; Found: C, 52.92; H, 5.72; N, 8.60. $C_{12}H_{16}N_2O$. 1.2 $(COOH)_2$ requires C, 53.20; H, 5.70; N, 8.62; δ(360 MHz, $D_2O$) 7.95 (1H, dd, J=7,8 Hz, py-H), 7.14 (1H, d, J=7 Hz, py-H), 6.97 (1H, d, J=8 Hz, py-H), 4.02 (3H, s, $OCH_3$), 4.00–3.30 (7H, m, $H_2$-2, H-4, $H_2$-6 and $H_2$-7), 1.95 (1H, m, H-5), 1.66 (1H, m, H-5); m/e 204 (M+).

EXAMPLE 33

2-Benzyloxycarbonyl-6-hydroxy-6-[2-(6methoxypyridin)yl]-2-azabicyclo[2.2.2]octane t-Butyl lithium (1.7M in pentane, 12.0 ml, 20.4 mmol) was added dropwise to a solution of 2-bromo-6-methoxypyridine [L. Testaferri et al, Tetrahedron (1985) 41 1373–1384] (1.92 g, 10.2 mmol) in ether (150 ml) cooled to −70°0 C. Afar 1 h, a solution of 2-benzyloxycarbonyl-2-azabicyclo[2.2.2]octan-6-one [prepared by analogy with the method of Low and Borne, Eur. J. Med. Chem. (1980) 15 229–235] (2.02 g, 7.8 mmol) in ether (30 ml), which had been dried over molecular sieves (4A) for 1 h, was added dropwise to the orange/red anion. The mixture was allowed to warm to −40° C. over 1 h and then quenched with ammonium chloride solution. The mixture was extracted with ether (×3), dried over magnesium sulphate and concentrated to a cream solid. Purification by chromatography through silica-gel using ethyl acetate/petrol (3:7), as eluent gave 0.84 g of the title compound as a white solid; m.p. 97°–98.5° C.; Found: C, 68.38; H, 6.71; N, 7.39. $C_{21}H_{24}N_2O_2$ requires C, 68.46; H, 6.57; N, 7:60; δ(360 MHz, $CDCl_3$) 3:2 mixture of rotomers, 7.50–6.56 (8H, Ph-H, H, pyridine-H), 5.10 (1H, br, OH), 4.99 and 4.70 (2H, m, $PhCH_2$), 3.92 and 3.89 (3H, s, $OCH_3$), 3.84 and 3.76 (1H, m, H-1), 3.53–3.35 (2H, m, $H_2$- 5), 2.50–1.60 (7H, m, H-4, $H_2$-5, $H_2$-7, $H_2$-8); $\nu_{max}$ (KBr) 3470s (OH), 1680s (C=O) $cm^{-1}$; m/e 368 (M+).

EXAMPLE 34

2-Benzyloxycarbonyl-6-chloro-6-[2-(6-methoxypyridin)yl]-2-azabicyclo[2.2.2]octane By the procedure described in Example 5, thionyl chloride (1.08 ml, 14.4 mmol) and 2-benzyloxycarbonyl-6-hydroxy-6-[2-(6-methoxypyridin)yl]-2-azabicyclo[2.2.2]octane (prepared as in Example 33, 1.77 g, 4.8 mmol) gave the crude product as a yellow oil. Purification by chromatography through silica-gel using ethyl acetate/peteol (1:9) as eluent gave 1.2 g of the title compound as a white solid; m.p. 90.5°–91.5° C.; Found: C, 65.14; H, 6.33; N, 7.26; Cl, 9.37. $C_{21}H_{23}ClN_2O_3$ requires C, 65.20; H, 5.99; N, 7.24; Cl, 9.16; δ(360 MHz, $CDCl_3$) 1:1 mixture of rotomers, 7.59–7.09 (7H, m, Ph-H, pyridine-H), 6.60 and 6.53 (1H, d, 0.5 Hz, pyridine-H), 4.90 and 4.69 (2H, d, J=12 Hz, $PhCH_2$), 4.59 and 4.39 (1H, m, H-1), 3.91 and 3.87 (3H, s, OCH₃), 3.75-1.56 (9H, m, H₂-3, H-4, H₂-5, H₂-7, H₂-8); m/e. (CI⁺) 387 (M+1).

EXAMPLE 35 a. 6-Chloro-6-[2-(6-methoxypyridin)yl]-2-azabicyclo[2.2.2]octane and b. 6-[2-(6-Methoxypyridin)yl]-2-azabicyclo[2.2.2]octane By the procedure described in Example 6, hydrogenation of 2-benzyloxycarbonyl-6-chloro-6-[2-(6-methoxypyridin)yl]-2-azabicyclo[2.2.2]octane (0.78 g, 2.0 mmol, prepared as in Example 34) gave a 2:7 mixture of the title compounds. Separation of the mixture by chromatography through silica-gel using dichloromethane/methanol/ammonia (89:10:1 ) as eluent gave first 0.08 g of 6-chloro-6-[2-(6-methoxypyridin)yl]-2-azabicyclo[2.2.2]octane as a colourless oil, followed by 0.27 g of 6[-2-(6-methoxypyridin)yl]-2-azabicyclo[2.2.2]octane as a cream solid; m.p. 152°-9° C.

6-Chloro-6-[2-(6-methoxypyridin)yl]-2-azabicyclo[2.2.2]octane was further characterised as the hydrogen oxalate salt; m.p. 150.5°-151.5° C.; δ(360 MHz, D₂O) 7.89 (1H, t, J=7.6 Hz, pyridine-H), 7.25 (1H, d, J=7.4 Hz, pyridine-H), 6.89 (1H, d, J=6.6 Hz, pyridine-H), 4.23 (1H, m, H-1), 3.93 (3H, s, OCH₃), 3.24 (2H, m, H₂-3), 2.39-1.80 (7H, m, H-4, H₂-5, H₂-7, H₂-8).

[2-(6-Methoxypyridin)yl]-2-azabicyclo[2.2.2]octane was further characterised as the tartrate salt; m.p. 157.5-158.5; δ(360 MHz, D₂O) 7.75 (1H, t, J=7 Hz, pyridine-H), 6.95 (1H, d, J=7 Hz, pyridine-H), 6.81 (1H, d, J=7 Hz, pyridine-H), 4.33 (1H, s, tartaric acid), 3.94 (3H, s. OCH₃), 3.74 (1H, m, H-1), 3.52 and 3.30 (3H, m, H₂-3 and H-6), 2.32-1.74 (7H, m, H-4, H₂-5, H₂-7 and H₂-8); m/e 218 (M+).

PHARMACEUTICAL EXAMPLES

1. Tablets containing 1-25 mg of compound (1)

|  | Amount-mg | | |
|---|---|---|---|
| Compound (1) | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

2. Tablets containing 26-100 mg of compound (1)

|  | Amount-mg | | |
|---|---|---|---|
| Compound (1) | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

Compound (1), lactose, and a portion of the corn starch are mixed together and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100.0 mg of compound (1) per tablet.

What we claim is:

1. A pyridine compound of Formula I below:

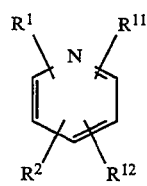

which is substituted on one of the ring carbon atoms with an $R^1$ azabicyclic ring substituent selected from the group consisting of

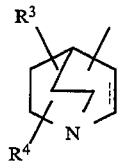

wherein the broken line represents a single or a double bond;

$R^3$ and $R^4$ independently represent hydrogen, $C_{1-4}$ alkyl, halo, $C_{1-4}$ alkoxy, hydroxy, carboxy or $C_{1-4}$ alkoxycarbonyl; or $R^3$ and $R^4$ together represent carbonyl;

$R^2$, $R^{11}$ and $R^{12}$ are each independently selected from the group consisting of hydrogen, halo, —CF₃, —OR⁶, —NR⁶R⁷, —NHOR⁶, —NHNH₂, —CN, COR⁸, and the hydrocarbon radicals: $C_1$–$C_{15}$ alkyl, $C_{2-15}$ alkenyl, $C_{2-15}$ alkynyl, aryl, aralkyl, which in turn are optionally substituted by halo, OR⁶, CF₃, NR⁶R⁷, —NO₂, keto, SR⁶, —SOR⁶, SO₂R⁶, CO₂R⁶, CONR⁶R⁷, wherein R⁶ is selected from the group consisting of hydrogen, $C_{1-6}$ alkyl, $C_{2-6}$ alkenyl and $C_{2-6}$ alkynyl; R⁷ is selected from the group consisting of hydrogen, $C_{1-6}$ alkyl and —COCH₃ and R⁸ is selected from the group consisting of —OR⁶ and —NR⁶R⁷; and pharmaceutically acceptable salts and prodrugs thereof, provided that the compound is neither 3-hydroxy-3-(2-pyridinyl)-1-azabicyclo[2.2.2]octane nor 3-(2-pyridinyl)-1-azabicyclo[2.2.2]oct-2 -ene.

2. A compound as claimed in claim 1 selected from the group consisting of:

3-[2-(6-chloropyridin)yl]-1-azabicyclo[2.2.2]octane;
3-[2-(6-dimethylaminopyridin)yl]-1-azabicyclo[2.2.2]octane;
3-[2-(6-methylpyridin)yl]-1-azabicyclo[2.2.2]octane;
3-[2-(6-methoxypyridin)yl]-1-azabicyclo[2.2.2]octane;
3-[3-(6-methoxypyridin)yl]-1-azabicyclo[2.2.2]octane;
3-(2-pyridinyl)-1-azabicyclo[2.2.2]octane;
3-(3-pyridinyl)-1-azabicyclo[2.2.2]octane;
3-(4-pyridinyl)-1-azabicyclo[2.2.2]octane;
6-[2-(6-methoxypyridin)yl]-2-azabicyclo[2.2.2]octane;
3-[2-(6-hydroxypyridin)yl]-1-azabicyclo[2.2.2]octane;
3-chloro-3-(2-pyridinyl)-1-azabicyclo[2.2.2]octane;
3-hydroxy-3-(3-pyridinyl)-1-azabicyclo[2.2.2]octane;
3-(3-pyridinyl)-1-azabicyclo[2.2.2]oct-2-ene;
3-hydroxy-3-[3-(6-methoxypyridin)yl]-1-azabicyclo[2.2.2]octane;
3-[3-(6-methoxypyridin)yl]-1-azabicyclo[2.2.2]oct-2-ene;
3-hydroxy-3-[3-(5-methoxypyridin)yl]-1-azabicyclo[2.2.2]octane;
3-[3-(5-methoxypyridin)yl]-1-azabicyclo[2.2.2]oct-2-ene;

3-[3-(5-methoxypyridin)yl]-1-azabicyclo[2.2.2]octane;
3-hydroxy-3-[3-(5-ethoxypyridin)yl]-1-azabicyclo[2.2.2]octane;
3-[3-(5-ethoxypyridin)yl]-1-azabicyclo[2.2.2]oct-2-ene;
3-[3-(5-ethoxypyridin)yl]-1-azabicyclo[2.2.2]octane;
3-hydroxy-3-[2-(6-methylpyridin)yl]-1-azabicyclo[2.2.2]octane;
3-[2-(6-methylpyridin)yl]-1-azabicyclo[2.2.2]oct-2-ene;
3-hydroxy-3-[2-(6-ethoxypyridin)yl]-1-azabicyclo[2.2.2]octane;
3-[2-(6-ethoxypyridin)yl]-1-azabicyclo[2.2.2]oct-2-ene;
3-[2-(6-ethoxypyridin)yl]-1-azabicyclo[2.2.2]octane;
3-hydroxy-3-[3-(4-methylpyridin)yl]-1-azabicyclo[2.2.2]octane;
3-[3-(4-methylpyridin)yl]-1-azabicyclo[2.2.2]oct-2-ene;
3-[3-(4-methylpyridin)yl]-1-azabicyclo[2.2.2]octane;
2-benzyloxylcarbonyl-6-hydroxy-6-[2-(6-methoxypyridin)yl]-2-azabicyclo[2.2.2]octane;
2-benzyloxycarbonyl-6-chloro-6-[2-(6-methoxypyridin)yl]-2-azabicyclo[2.2.2]octane;
6-chloro-6-[2-(6-methoxypyridin)yl]-2-azabicyclo[2.2.2]octane;
6-[2-(6-methoxypyridin)yl]-2-azabicyclo[2.2.2]octane;
and pharmaceutically acceptable salts thereof.

3. A pharmaceutical composition comprising a therapeutically effective amount of compound as claimed in claim 1 in association with a pharmaceutically acceptable carrier therefor.

4. A pharmaceutical composition comprising 3-(2-pyridinyl)-1azabicyclo[2.2.2]oct-2-ene in an effective amount as the active ingredient and a pharmaceutically acceptable carrier therefor.

5. A method for the treatment of neurological or mental disorders, said method comprises the administration to a patient in need of such treatment a therapeutically effective amount of a compound as defined in claim 1, or 3-(2-pyridinyl)-1-azabicyclo]oct-2-ene, or mixture thereof.

6. The compound according to claim 1 wherein $R^1$ is attached to the pyridine ring at the 3'-carbon position of $R^1$; $R^2$ is selected from the group consisting of hydrogen, halo, —$OR^6$, —$NR^6R^7$ and $C_{1-6}$alkyl; and $R^{11}$ and $R^{12}$ are each hydrogen.

7. The compound according to claim 1 wherein the azabicycle is either unsubstituted or substituted at the 3' position by a substituent selected from the group consisting of halogen.

8. The compound according to claim 1 wherein $R^1$ is selected from the group consisting of:

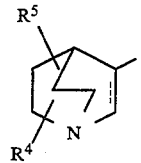

and $R^3$ and $R^4$ are each independently selected from the group consisting of hydrogen, halo and hydroxy; other than 3-hydroxy-3-(2-pyridinyl)-1-azabicyclo[2.2.2]octane and 3-(2-pyridinyl)-1-azabicyclo[2.2.2]oct-2-ene.

* * * * *

UNITED STATES PATENT AND TRADEMARK OFFICE
CERTIFICATE OF CORRECTION

PATENT NO. : 5,346,906
DATED : September 13, 1994
INVENTOR(S) : Raymond Baker, etal.

It is certified that error appears in the above-indentified patent and that said Letters Patent is hereby corrected as shown below:

At Column 23, in claim 4, please replace line 30, which reads "pyridinyl)-1azabicyclo[2.2.2]oct-2-ene in an effective" with -- pyridinyl)-1-azabicyclo[2.2.2]oct-2-ene in an effective --.

Signed and Sealed this

Thirtieth Day of May, 1995

Attest:

BRUCE LEHMAN

*Attesting Officer*      *Commissioner of Patents and Trademarks*